(12) United States Patent
Deckner et al.

(10) Patent No.: US 9,393,188 B2
(45) Date of Patent: *Jul. 19, 2016

(54) ORAL COMPOSITIONS CONTAINING GEL NETWORKS

(71) Applicant: The Procter & Gamble Company, Cincinnati, OH (US)

(72) Inventors: George Endel Deckner, Cincinnati, OH (US); Arif Ali Baig, Mason, OH (US); Michael Jude LeBlanc, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,786

(22) Filed: Mar. 10, 2015

(65) Prior Publication Data

US 2015/0174039 A1    Jun. 25, 2015

Related U.S. Application Data

(63) Continuation of application No. 11/904,692, filed on Sep. 28, 2007.

(60) Provisional application No. 60/848,335, filed on Sep. 29, 2006.

(51) Int. Cl.
| | | |
|---|---|---|
| *A61K 8/69* | (2006.01) | |
| *A61K 8/04* | (2006.01) | |
| *A61K 8/34* | (2006.01) | |
| *A61K 8/44* | (2006.01) | |
| *A61K 8/46* | (2006.01) | |
| *A61K 8/49* | (2006.01) | |
| *A61K 8/55* | (2006.01) | |
| *A61Q 11/00* | (2006.01) | |
| *A61K 8/38* | (2006.01) | |
| *A61K 8/18* | (2006.01) | |

(52) U.S. Cl.
CPC . *A61K 8/69* (2013.01); *A61K 8/042* (2013.01); *A61K 8/342* (2013.01); *A61K 8/345* (2013.01); *A61K 8/38* (2013.01); *A61K 8/44* (2013.01); *A61K 8/442* (2013.01); *A61K 8/463* (2013.01); *A61K 8/466* (2013.01); *A61K 8/4926* (2013.01); *A61K 8/553* (2013.01); *A61Q 11/00* (2013.01); *A61K 2800/59* (2013.01)

(58) Field of Classification Search
None
See application file for complete search history.

(56) References Cited

U.S. PATENT DOCUMENTS

| | | |
|---|---|---|
| 3,894,147 A | 7/1975 | Bahouth |
| 4,666,517 A | 5/1987 | Bakar |
| 5,093,112 A | 3/1992 | Birtwistle |
| 5,424,060 A | 6/1995 | Hauschild |
| 5,512,278 A | 4/1996 | Mundschenk |
| 6,113,884 A | 9/2000 | Mirajkar et al. |
| 6,303,109 B1 | 10/2001 | Foerster |
| 6,346,235 B1 | 2/2002 | Joziak et al. |
| 6,534,456 B2 | 3/2003 | Hayward |
| 6,599,513 B2 | 7/2003 | Deckers |
| 6,682,717 B1 | 1/2004 | Wills et al. |
| 6,794,347 B2 | 9/2004 | Hsu |
| 7,018,970 B2 | 3/2006 | Hsu |
| 9,005,585 B2 * | 4/2015 | Deckner ............. A61K 8/042 424/49 |
| 2003/0223952 A1 | 12/2003 | Wells |
| 2005/0031659 A1 | 2/2005 | Deckner |
| 2005/0152851 A1 | 7/2005 | Kaminski |
| 2006/0024248 A1 | 2/2006 | Spengler |
| 2006/0024256 A1 | 2/2006 | Wells |
| 2006/0127345 A1 | 6/2006 | Hilvert |
| 2006/0210491 A1 | 9/2006 | Behan |
| 2006/0269501 A1 | 11/2006 | Johnson |
| 2007/0048339 A1 | 3/2007 | Popplewell |
| 2007/0110700 A1 | 5/2007 | Wells |
| 2008/0026111 A1 | 1/2008 | Bellody |

FOREIGN PATENT DOCUMENTS

| | | |
|---|---|---|
| EP | 0348560 | 1/1990 |
| JP | 08169813 | 7/1996 |
| JP | 2003286145 | 10/2003 |
| JP | 2005289917 | 10/2005 |
| WO | WO 0015180 | 3/2000 |

OTHER PUBLICATIONS

PCT International Search Report and Written Opinion, Int'l Appl. No. PCT/US2007/020979, mailing date Mar. 27, 2008.
System 3 Formulation Guidelines, prepared by Collaborative Laboratories, 2009.

* cited by examiner

*Primary Examiner* — Brian Gulledge
(74) *Attorney, Agent, or Firm* — Alexandra S. Anoff

(57) ABSTRACT

The present invention is directed to an oral composition containing a gel network phase comprising: (i) one or more fatty amphiphiles, (ii) one or more surfactants, and (iii) one or more solvents; and an oral carrier phase. In certain embodiments, the gel network is used to structure the oral composition. The present invention is also directed to a method of forming an oral composition containing a gel network.

23 Claims, No Drawings

ORAL COMPOSITIONS CONTAINING GEL NETWORKS

FIELD OF THE INVENTION

The present invention relates to an oral composition containing a gel network.

BACKGROUND OF THE INVENTION

The rheology of oral care composition, particularly dentifrices, is very challenging to formulate. The composition must not be too thick so it can easily dispense out of a tube but thick enough to stand up on a toothbrush without sinking into the bristles. The viscosity of the oral composition must remain stable over time as not to continue to thicken so the oral composition remains easy to dispense during the shelf life. Once dispensed from a container, the oral composition should not be stringy or sticky as to be messy for a consumer to use. The oral composition must also easily disperse once in the mouth and create a foam. It is also desired that the oral composition not stick to a sink or leave difficult to remove hard dried residue. In addition to balancing the viscosity and shear thinning to formulate acceptable rheology, the oral composition must also be stable and keep actives ingredients, such as fluoride, available.

In addition to the above requirement for a consumer desired oral composition, it is also desired that oral composition be relatively easy to process. The oral composition must have the desired rheology and shelf stability as described above but also be viscous enough to quickly fill the oral composition into a container. It is also desired that the process not require special equipment and that the time to process not be long. Typically, oral compositions are thickened with a polymeric thickener. Polymeric thickeners may require a hydration step which can limit processing flexibility and cause aeration problems. It is also desired that the thickening system of an oral composition be low cost and comprise commonly available ingredients.

Based on the foregoing, there is a need for continuously improved thickening or structuring systems for oral compositions. None of the existing art provides all of the advantages and benefits of the present invention.

SUMMARY OF THE INVENTION

The present invention is directed to an oral composition containing a gel network phase comprising: (i) one or more fatty amphiphiles, (ii) one or more secondary surfactants, and (iii) one or more solvents; and an oral carrier phase. The gel network phase can be used to structure the oral composition. In some embodiments, the oral composition is a dentifrice or a concentrated dentifrice. The fatty amphiphile can be a single fatty alcohol or a combination of fatty alcohols, such as cetyl alcohol and stearyl alcohol. Optionally, a surfactant, such as sodium lauryl sulfate, can be added to the oral carrier phase in addition to the secondary surfactant being in the gel network phase. The gel network phase may provide the desired rheology without the use of a thickening agent but optionally, a thickening agent may still be used. The thickening agents may be used in a thickening amount or the oral composition may be essentially free of thickening agents. The oral composition may contain more than one gel network, such as a gel network for delivery or sequestration of non-compatible materials. The present invention is further directed to a method of using an effective amount of the oral composition in the oral cavity.

The present invention also is directed to a process of making the oral composition described above. In one method of making the oral composition, a fatty amphiphile, secondary surfactant, and solvent are combined at a temperature sufficient to allow partitioning of the secondary surfactant and solvent into the fatty amphiphile. This mixture is then cooled below the chain melt temperature of the fatty amphiphile to form a gel network. Once the gel network is formed, oral carrier materials are added to the gel network to form the oral composition. Optionally, some oral carrier materials may be added with the materials for the gel network or may be added when the gel network materials are cooling. An additional surfactant may be post-added, meaning added after the gel network is formed.

These and other features, aspects, and advantages of the present invention will become evident to those skilled in the art from a reading of the present disclosure.

DETAILED DESCRIPTION OF THE INVENTION

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan.

By "oral composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition of the present invention may be in various forms including toothpaste, dentifrice, tooth gel, liquid gel, subgingival gel, foam, mouse, or denture product. The oral composition may also be a rinse thickened by a gel network. The oral composition may also be incorporated onto strips or films for direct application or attachment to oral surfaces.

The term "dentifrice", as used herein, means paste, gel, powder, or liquid formulations unless otherwise specified, used to clean the surfaces of the oral cavity. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, package, or container suitable for dispensing oral compositions.

The term "teeth", as used herein, refers to natural teeth as well as artificial teeth or dental prosthesis.

The term "polymer" as used herein shall include materials whether made by polymerization of one type of monomer or made by two (i.e., copolymers) or more types of monomers.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The term "secondary surfactant" as used herein means a surfactant other than a fatty amphiphile. Various types of suitable surfactants are listed below. There may be more than one secondary surfactants. There will be at least one secondary surfactant in the gel network phase. There may be another surfactant in the oral carrier phase.

The oral compositions of the present invention comprise a dispersed gel network phase and an oral carrier phase. To the naked eye, the dispersed gel network phase and the oral carrier phase cannot be distinguished. The phases are immiscible within each other. However, components of each phase, particularly water soluble components, may migrate to the other phase. For example, a secondary surfactant is required in the gel network phase but a portion of the secondary surfactant may migrate to the oral carrier phase. Similarly, a flavor added to the oral carrier phase may migrate to the gel network phase. Each of the essential components, as well as preferred or optional components, is described in detail hereinafter.

A. Gel Network

The oral compositions of the present invention comprise a dispersed gel network phase comprising a fatty amphiphile. As used herein, the term "gel network" refers to a lamellar or vesicular solid crystalline phase which comprises at least one fatty amphiphile as specified below, at least one secondary surfactant as specified below, and a solvent as specified below. The lamellar or vesicular phase comprises bi-layers made up of a first layer comprising the fatty amphiphile and the secondary surfactant and alternating with a second layer comprising the solvent. For the lamellar crystalline phase to form, the fatty amphiphile and secondary surfactant must be dispersed within the solvent. The term "solid crystalline", as used herein, refers to the structure of the lamellar or vesicular phase which forms at a temperature below the chain melt temperature of the layer in the gel network comprising the one or more fatty amphiphiles. The chain melt temperature may be measured by differential scanning calorimetry, a method of which is described in the Examples below.

The gel network in the oral composition is used to structure the oral composition. The structuring provided by the gel network provides the desired rheology or viscosity by thickening the oral composition. The structuring can be done without the need for polymeric thickening agents, however, polymeric thickeners or other agents could be used in addition to the gel network to structure the oral composition.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol.* 7, 63-70 (1986).

According to this embodiment of the present invention, the gel network component of the present invention may be prepared by heating the fatty amphiphile, the secondary surfactant, and solvent to a level in the range of about 50° C. to about 90° C. and mixing. This mixture is cooled to a level in the range of about 20° C. to about 35° C. by, for example, passing the mixture through a heat exchanger. As a result of this cooling step, the fatty amphiphile and the secondary surfactant crystallize to form a solid crystalline gel network. The oral carriers can be added at any time during this process.

Alternative methods of preparing the gel network component include sonication and/or milling of the fatty amphiphile, the secondary surfactant, and solvent, while these components are heated, to reduce the particle size of the melted fatty amphiphile phase. This results in an increase in surface area of the fatty amphiphile phase, which allows the secondary surfactant and the solvent to swell the fatty amphiphile phase. Another suitable variation in preparing the gel network includes heating and mixing the fatty amphiphile and the secondary surfactant first, and then adding that mixture to the solvent.

An equilibrated lamellar dispersion ("ELD") is formed in the final oral composition. The ELD is a dispersed lamellar or vesicular phase resulting from the gel network component substantially equilibrating with oral carriers and other optional components.

The presence of the gel network in the oral composition in the form of the ELD can be confirmed by means known to one of skill in the art, such as X-ray analysis, optical microscopy, electron microscopy, and differential scanning calorimetry. Methods of X-ray analysis and differential scanning calorimetry are described in the Examples below.

In an embodiment of the present invention, the weight ratio of the fatty amphiphile to the surfactant in the gel network component is greater than about 1:5, preferably from about 1:3 to about 100:1, more preferably greater than about 1:1 to about 20:1, and even more preferably greater than about 2:1 to about 10:1.

1. Fatty Amphiphile

The gel network component of the present invention comprises at least one fatty amphiphile. As used herein, "fatty amphiphile" refers to a compound having a hydrophobic tail group of $R_1$ as defined below and a hydrophilic head group which does not make the compound water soluble (immiscible), wherein the compound also has a net neutral charge at the pH of the oral composition. The term "water soluble", as used herein, means that the material is soluble in water in the present composition. In general, the material should be soluble at 25° C. at a concentration of 0.1% by weight of the water solvent, preferably at 1%, more preferably at 5%, more preferably at 15%.

The fatty amphiphile of the present invention may be characterized as a compound having a Hydrophilic-Lipophilic Balance ("HLB") of 6 or less. The HLB, as used herein, is the standard HLB according to Griffin, J. Soc. Cosm. Chem., vol. 5, 249 (1954).

The oral compositions of the present invention comprise fatty amphiphile in an amount from about 0.05% to about 30%, preferably from about 0.1% to about 20%, and more preferably from about 0.5% to about 10%, by weight of the oral composition. The amount of fatty amphiphile will be chosen based on the formation of the gel network and the composition of the oral formulation. For example, an oral composition containing low amounts of water may require about 1% of a fatty amphiphile whereas an oral composition with higher amounts of water may require 6% or more of a fatty amphiphile.

According to the present invention, suitable fatty amphiphiles, or suitable mixtures of two or more fatty amphiphiles, preferably have a melting point of at least about 45° C. In some embodiments, it is preferred that the melting point be at least about 50 C or greater than about 55 C or greater than about 60 C. The melting point, as used herein, may be measured by a standard melting point method as described in U.S. Pharmacopeia, USP—NF General Chapter <741>"Melting range or temperature". The melting point of a mixture of two or more materials is determined by mixing the two or more materials at a temperature above the respective melt points and then allowing the mixture to cool. If the resulting composite is a homogeneous solid below about 45° C., then the mixture has a suitable melting point for use in the present invention. A mixture of two or more fatty amphiphiles, wherein the mixture comprises at least one fatty amphiphile having an individual melting point of less than about 45° C., still is suitable for use in the present invention provided that the composite melting point of the mixture is at least about 45° C.

According to the present invention, suitable fatty amphiphiles have a hydrophobic tail group of $R_1$. As used herein, $R_1$ is an alkyl, alkenyl (containing up to 3 double bonds), alkyl aromatic, or branched alkyl group of $C_{12}$-$C_{70}$ length. Non-limiting examples of alkyl, alkenyl, or branched alkyl groups suitable for the fatty amphiphiles of the present invention include lauryl, tridecyl, myristyl, pentadecyl, cetyl, heptadecyl, stearyl, arachidyl, behenyl, undecylenyl, palmitoleyl, oleyl, palmoleyl, linoleyl, linolenyl, arahchidonyl, elaidyl, elaeostearyl, erucyl, isolauryl, isotridecyl, isomyristal, isopentadecyl, petroselinyl, isocetyl, isoheptadecyl, isostearyl, isoarachidyl, isobehnyl, gadoleyl, brassidyl, and technical-grade mixture thereof.

As used herein, $R_1$ also may be a branched alkyl group prepared by alkaline condensation of alcohols to give higher molecular weight, branched isoalcohols. These branched isoalcohols are referred to in the art as Guerbet alcohols.

$R_1$ may be alkyl, alkenyl or branched carbon chains of vegetable origin, such as wheat germ, sunflower, grape seed, sesame, maize, apricot, castor, avocado, olive, soybean, sweet almond, palm, rapeseed, cotton seed, hazelnut, macadamia, karite, jojoba, alfalfa, poppy, pumpkinseed, sesame, cucumber, blackcurrant, evening primrose, millet, barley, quinoa, rye, safflower, candlenut, passion flower or musk rose oil, and karite butter.

Suitable fatty amphiphiles of the present invention also have a hydrophilic head group which does not make the compound water soluble, such as in compounds having an HLB of 6 or less. Non-limiting examples of classes of compounds having such a hydrophilic head group include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids.

To form the gel network component of the present invention, individual fatty amphiphile compounds or combinations of two or more different fatty amphiphile compounds may be selected. The following provides non-limiting examples of classes of compounds from which one or more fatty amphiphiles suitable for use in the present invention may be selected.

a. Fatty Alcohols/Alkoxylated Fatty Alcohol Ethers

Fatty amphiphiles of the present invention may be selected from fatty alcohol compounds or alkoxylated fatty alcohol ether compounds according to the following formula:

wherein $R_1$ is as described above; $R_2$ is a $C_1$-$C_5$ carbon chain which may be branched or hydroxy substituted; and k is a number ranging from about 0 to about 5.

The fatty alcohols useful herein are those having from about 12 to about 60 carbon atoms, preferably from about 16 to about 60 carbon atoms. These fatty alcohols may be straight or branched chain alcohols and may be saturated or unsaturated. Non-limiting examples of suitable fatty alcohols include cetyl alcohol, stearyl alcohol, arachidyl alcohol, behenyl alcohol, eicosyl alcohol, C20-40 alcohols, C30-50 alcohols, C40-60 alcohols, and mixtures thereof.

Suitable alkoxylated fatty alcohol ethers include addition products of 1 to 5 mol of ethylene oxide with a linear fatty alcohol having about 12 to about 60 carbon atoms, which are all adducts obtainable by the known industrial oxyethylation processes. Also suitable are the polyethylene oxide condensates of alkyl phenols, for example, the condensation products of alkyl phenols having an alkyl group containing from about 12 to about 60 carbon atoms in either a straight chain or branched chain configuration, with ethylene oxide, wherein the ethylene oxide is present in amounts equal to from about 1 to about 5 moles of ethylene oxide per mole of alkyl phenol. Further suitable alkoxylated fatty alcohol ethers include those derived from the condensation of ethylene oxide with the product resulting from the reaction of propylene oxide and ethylene diamine products.

Non-limiting examples of suitable alkoxylated fatty alcohol ethers include steareth-2, beheneth-2, beheneth-5, beheneth-10, C20-40 Pareth-3, C20-40 Pareth-10, C30-50 Pareth-3, and C30-50-Pareth-10.

In one embodiment, a combination of fatty alcohols such as cetyl and stearyl alcohol is preferred. The ratio of cetyl to stearyl alcohol can be from about 4:1 to about 1:4, preferably from about 2:1 to about 1:2, and in some embodiments 1:1.

b. Di-Fatty Ethers

Fatty amphiphiles of the present invention may be selected from di-fatty ether compounds according to the following formula:

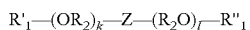

wherein $R_1$ is as described above; $R_2$ is a $C_1$-$C_5$ carbon chain which can be branched or hydroxy substituted; k and l each is independently a number such that the sum (k+l) has a value ranging from 1 to 30; and Z is an ether (i.e., —O—) or an amine (i.e., —$NR_2$—, wherein $R_2$ is as described immediately above).

Compounds of the above formula in which Z is an ether (i.e., dialkyl oxyethyl ethers) may be prepared by esterification processes, which are known in the art, of fatty alcohols and fatty alkyl oxyethanols. Compounds of the above formula in which Z is an amine group may be obtained, for example, from triethanolamine by O-alkylation with 2 mol of a sulfuric half-ester salt of a $C_{12}$-$C_{60}$ fatty alcohol, according to a process for the preparation of ether amines described in DE 35 04 242.

Non-limiting examples of suitable di-fatty ether compounds include dicetylstearyl ether, dicetylstearyl dioxyethyl ether, and N,N-bis(2-cetylstearyl-oxyethyl)aminoethanol.

c. Fatty Amides/Fatty Alkanolamides/Fatty Alkoxylated Amides

Fatty amphiphiles of the present invention also may be selected from fatty amide compounds according to the following formula:

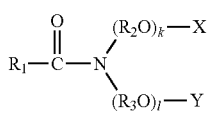

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y are each independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty amides, fatty alkanolamides or fatty alkoxylated amides include Cocamide, Cocamide Methyl MEA, Cocoyl Glutamic Acid, Erucamide, Lauramide, Oleamide, Palmitamide, Stearamide, Stearyl Erucamide, Behenamide DEA, Behenamide MEA, Cocamide DEA, Cocamide MEA, Cocamide MIPA, Hydroxyethyl Stearamide-MIPA, Hydroxypropyl Bisisostearamide MEA, Hydroxypropyl Bislauramide MEA, Hydroxystearamide MEA, Isostearamide DEA, Isostearamide MEA, Isostearamide MIPA, Lauramide DEA, Lauramide MEA, Lauramide MIPA, Myristamide DEA, Myristamide MEA, Myristamide MIPA, Palmamide DEA, Palmamide MEA, Palmamide MIPA, Palmitamide DEA, Palmitamide MEA, PEG-20 Cocamide MEA, Stearamide AMP, Stearamide DEA, Stearamide DEA-Distearate, Stearamide DIBA-Stearate, Stearamide MEA, Stearamide MEA-Stearate, Stearamide MIPA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PEG-9 Oleamide, PEG-4 Stearamide, PEG-10 Stearamide, PPG-2 Cocamide, PPG-2 Hydroxyethyl Cocamide, PPG-2 Hydroxyethyl Coco/Isostearamide, Ceramide 1, Ceramide 2, Ceramide 3, Ceramide 4, and Ceramide 5.

d. Fatty Carbamates

Fatty amphiphiles of the present invention may be selected from fatty carbamate compounds according to the following formula:

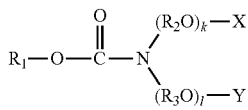

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; and X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage.

Non-limiting examples of suitable fatty carbamates include cetyl carbamate, stearyl carbamate, PEG-2 stearyl carbamate, PEG-4 stearyl carbmate, and behenyl carbamate.

e. Fatty Alkylamido Alkylamines

Fatty amphiphiles of the present invention also may be selected from fatty alkylamido alkylamine compounds according to the following formula:

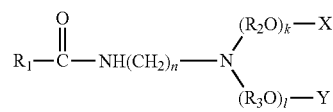

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently selected from hydrogen, a $C_1$-$C_4$ carbon chain which can be branched or hydroxy substituted, morpholine, or a $C_5$-$C_{50}$ carbon chain bonded via an amide, ester, or ether linkage; and n is a number ranging from about 1 to about 4.

Non-limiting examples of suitable fatty alkylamido alkylamine compounds include stearamidoethyl diethanolamine, stearamidopropyl morpholine, stearamidopropyl dimethylamine stearate, stearamidopropyl dimethylamine, stearamidoethyl diethylamine, stearamidoethyl diethanolamine, isostearamidomorpholine stearate behenamidopropyldimethyl amine, behenamidopropyldiethylamine, behenamidoethyldiethyl-amine, cocamidopropyl dimethylamine behenamidoethyldimethylamine, arachidamidopropyldimethylamine, arachidamido-propyidiethylamine, arachidamidoethyidiethylamine, arachidamidoethyidimethylamine, and mixtures thereof.

f. Fatty Amines/Fatty Alkanolamines/Fatty Alkoxylated Amines

Fatty amphiphiles of the present invention further may be selected from fatty amine compounds according to the following formula:

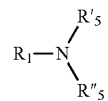

wherein $R_1$ is as described above; and $R'_5$ and $R''_5$ are independently hydrogen or a $C_1$-$C_5$ carbon chain which can be branched or hydroxy substituted.

Additionally, fatty amphiphiles of the present invention may be selected from fatty alkoxylated amine compounds according to either one of the following formulas:

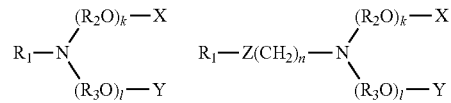

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via amide, ester, or ether linkage; n is a number ranging from about 1 to about 4; and Z is an ether (i.e., —O—) or an amine (i.e., —NH—).

Primary, secondary, and tertiary fatty amines are useful. Suitable fatty alkoxylated amine compounds include addition products of ethylene oxide with a linear fatty alkylamine having 12 to 60 carbon atoms, all of which are adducts obtainable by known industrial processes and which are commercially available.

Non-limiting examples of suitable fatty amine and fatty alkoxylated amine compounds include diethyllauramine, dicocamine, dimethylcocamine amine cetamine, stearamine, oleamine, behenamine, dimethylbehenamine amine, diethylbehenamine, dibehenylamine N-lauryl diethanolamine. TEA-diricinoleate, TEA-lauryl ether, diethylaminoethyl PEG-5 cocoate, diethylaminoethyl PEG-5 laurate, hydroxyethyl isostearyloxy isopropanolamine, PEG-2 cocamine, PEG-5 cocamine, PEG-10 cocamine, PEG-5 isodecyloxypropylamine, PEG-2 lauramine, PEG-2 oleamine, PEG-5 oleamine, PEG-10 oleamine, PEG-2 stearamine, PEG-5 stearamine, PEG-10 stearamine, PPG-2 cocamine, PPG-2 hydrogenated tallowamine, PPG-2 tallowamine, and PPG-3 tallow aminopropylamine.

g. Fatty Amine Oxides

Fatty amphiphiles of the present invention also may be selected from fatty amine oxide compounds according to the following formula:

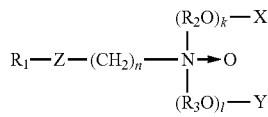

wherein $R_1$ is as described above; $R_2$ and $R_3$ each is independently a $C_1$-$C_5$ carbon chain which can be branched or hydroxy substituted; k and l each is independently a number such that the sum (k+l) has a value ranging from 0 to 10; X and Y each is independently hydrogen, a $C_1$-$C_4$ carbon chain which can be branched or hydroxy substituted, morpholine, or a $C_5$-$C_{50}$ carbon chain bonded via an amide, ester, or ether linkage; Z is an ether (i.e., —O—) or an amide (i.e., —C(O)—NH—) linkage; and n is a number ranging from about 1 to about 4. In accord with known convention, the arrow in the above formula is representative of a semi-polar bond.

Non-limiting examples of suitable amine oxide compounds include dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl C12-15 alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl C12-15 alkoxypropylamine oxide, lauramine oxide, myristamine oxide, myristyl/cetyl amine oxide, oleamidopropylamine oxide, oleamine oxide, palmitamine oxide, PEG-3 lauramine oxide, potassium trisphosphonomethylamine oxide, stearamine oxide, and tallowamine oxide.

h. Fatty Acid/Alkoxylated Fatty Acid

Fatty amphiphiles of the present invention also may be selected from fatty acid or alkoxylated fatty acid compounds according to the following formula:

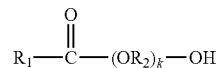

wherein $R_1$ is as described above; $R_2$ is a $C_1$-$C_5$ carbon chain which can be branched or hydroxy substituted; and k is a number ranging from about 0 to about 5.

Non-limiting examples of suitable fatty acids and alkoxylated fatty acids include behenic acid, C10-40 hydroxyalkyl acid, C32-36 isoalkyl acid coconut acid, erucic acid, hydroxystearic acid, lauric acid, linoleic acid, myristic acid, oleic acid, palmitic acid, PEG-8 behenate, PEG-5 cocoate, PEG-10 cocoate, PEG-2 laurate, PEG-4 laurate PEG-6 laurate, PEG-8 laurate, PEG-9 laurate, PEG-10 laurate, PEG-7 oleate, PEG-2 stearate, PEG-3 stearate, PEG-4 stearate, PEG-5 stearate, PEG-6 stearate, PEG-7 stearate, PEG-8 stearate, PEG-9 stearate, PEG-10 stearate, polyglyceryl-2-PEG-4 stearate, PPG-2 isostearate, and PPG-9 laurate.

i. Fatty Esters

Fatty amphiphiles of the present invention may be selected from fatty ester compounds according to the following formula:

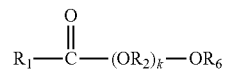

wherein $R_1$ is as described above; $R_2$ is a $C_1$-$C_5$ carbon chain which can be branched or hydroxy substituted; k is a number ranging from about 1 to about 5; and $R_6$ is a $C_1$-$C_{40}$ carbon chain or an alkylcarbonyl (i.e.,

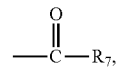

wherein $R_7$ is a $C_1$-$C_{40}$ carbon chain).

These suitable fatty esters include esters with hydrocarbyl chains derived from fatty acids or alcohols (e.g., mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Non-limiting examples of suitable fatty ester compounds include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Fatty amphiphiles of the present invention also may be selected from other fatty ester compounds according to the following formula:

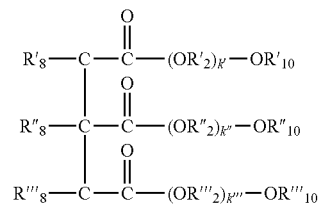

wherein $R'_8$, $R''_8$, and $R'''_8$ each is independently selected from hydrogen, hydroxy, or a $C_1$-$C_4$ carbon chain which can be branched or hydroxy substituted; k', k'', and k''' each is independently a number such that the sum (k'+k''+k''') has a value ranging from 0 to 15; $R'_2$, $R''_2$, and $R'''_2$ each is independently selected from a $C_1$-$C_5$ carbon chain which can be branched or hydroxy substituted; and where $R'_{10}$, $R''_{10}$, $R'''_{10}$ each is independently selected form hydrogen or $R_1$, where $R_1$ is as defined above, provided that at least one of $R'_{10}$, $R''_{10}$, and $R'''_{10}$ is a R1 group.

Still other suitable fatty esters are di- and tri-alkyl and alkenyl esters of carboxylic acids, such as esters of $C_4$ to $C_8$ dicarboxylic acids (e.g., $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, stearyl citrate, distearyl citrate and tristearyl citrate.

Fatty amphiphiles of the present invention further may be selected from other fatty ester compounds according to the following formula:

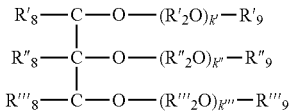

wherein $R'_2$, $R''_2$, and $R'''_2$ each is independently selected from a $C_1$-$C_5$ carbon chain which can be branched or hydroxy substituted; $R'_8$, $R''_8$, and $R'''_8$ each is independently selected from hydrogen, hydroxy, or $C_1$-$C_4$ carbon chain which can be branched or hydroxy substituted; k', k'', and k''' each is independently a number such that the sum (k'+k''+k''') has a value ranging from 0 to 15; and $R'_9$, $R''_9$, and $R'''_9$ each is independently selected from hydrogen or alkylcarbonyl (i.e.,

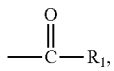

wherein $R_1$ is as described above), provided that at least one of $R'_9$, $R''_9$, and $R'''_9$ is a

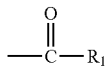

group.

Other suitable fatty esters are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester.

Still other fatty esters suitable for use in the compositions of the present invention are glycerides, including, but not limited to, mono-, di-, and tri-glycerides, preferably mono- and di-glycerides, more preferably mono-glycerides. For use in the compositions described herein, the glycerides are preferably the mono-, di-, and tri-esters of glycerol and long chain carboxylic acids, such as $C_{12}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

j. Fatty Phosphorus Compounds

Fatty amphiphiles of the present invention may be selected from fatty phosphorus compounds according to the following formula:

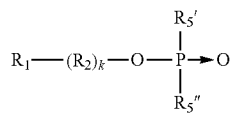

wherein $R_1$ is as described above; $R_2$ is a $C_1$-$C_5$ carbon chain which can be branched or hydroxy substituted; k is a number ranging from about 0 to about 5; and $R_5$ is hydrogen or a $C_1$-$C_4$ carbon chain which can be branched or hydroxy substituted. In accord with known convention, the arrow in the above formula is representative of a semi-polar bond.

Non-limiting examples of suitable fatty phosphorus compounds include dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl) phosphine oxide, tetradecylmethyl-2-hydroxypropylphosphine oxide, oleyldimethylphosphine oxide, and 2-hydroxydodecyldimethylphosphine oxide.

k. Fatty Sorbitan Derivatives

Fatty amphiphiles of the present invention also may be selected from fatty sorbitan derivative compounds according to the following formula:

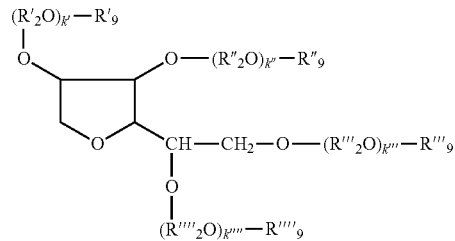

wherein $R'_2$, $R''_2$, $R'''_2$, and $R''''_2$, each is independently a $C_1$-$C_5$ carbon chain which can be branched or hydroxy substituted; $R'_9$, $R''_9$, $R'''_9$, and $R''''_9$ each is independently hydrogen or alkylcarbonyl (i.e.,

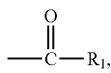

wherein $R_1$ is as described above), provided that at least one of $R'_9$, $R''_9$, $R'''_9$, and $R''''_9$ is a

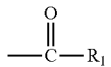

group; and k', k'', k''', and k'''' each is independently a number such that the sum (k'+k''+k'''+k'''') has a value ranging from 0 to 20.

Non-limiting examples of suitable fatty sorbitan derivatives include PEG-20 sorbitan cocoate, PEG-2 sorbitan isostearate, PEG-5 sorbitan isostearate, PEG-20 sorbitan isostearate, PEG-10 sorbitan laurate, PEG-3 sorbitan oleate, PEG-6 sorbitan oleate, PEG-20 sorbitan oleate, PEG-3 sorbitan stearate, PEG-4 sorbitan stearate, PEG-6 sorbitan stearate, PEG-20 sorbitan stearate, PEG-4 sorbitan triisostearate, PEG-20 sorbitan triisostearate, PEG-2 sorbitan trioleate, PEG-3 sorbitan tristearate, polyglyceryl-2 sorbitan tetraethylhexanoate, sorbitan caprylate, sorbitan cocoate, sorbitan diisostearate, sorbitan dioleate, sorbitan distearate, sorbitan isostearate, sorbitan laurate, sorbitan oleate, sorbitan olivate, sorbitan palmitate, sorbitan sesquiisostearate, sorbitan sesquioleate, sorbitan sesquistearate, sorbitan stearate, sorbitan triisostearate, sorbitan trioleate, sorbitan tristearate, and sorbitan undecylenate.

1. Sucrose Polyesters

Fatty amphiphiles of the present invention may be selected from sucrose polyester compounds according to the following formula:

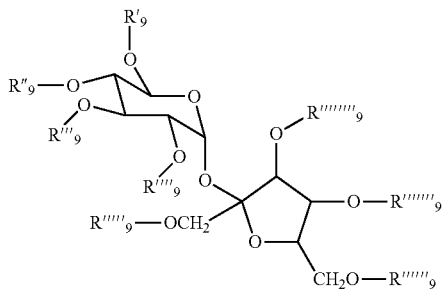

wherein $R'_9$, $R''_9$, $R'''_9$, $R''''_9$, $R'''''_9$, $R''''''_9$, $R'''''''_9$, and $R''''''''_9$ each is hydrogen or alkylcarbonyl (i.e.,

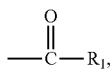

wherein $R_1$ is as described above), provided that at least one of $R'_9$, $R''_9$, $R'''_9$, $R''''_9$, $R'''''_9$, $R''''''_9$, $R'''''''_9$, and $R''''''''_9$ is a

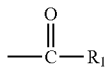

group.

Non-limiting examples of suitable sucrose polyester compounds include Sucrose Cocoate, Sucrose Dilaurate, Sucrose Distearate, Sucrose Hexaerucate, Sucrose Hexaoleate/Hexapalmitate/Hexastearate, Sucrose Hexapalmitate, Sucrose Laurate, Sucrose Mortierellate, Sucrose Myristate, Sucrose Octaacetate, Sucrose Oleate, Sucrose Palmitate, Sucrose Pentaerucate, Sucrose Polybehenate, Sucrose Polycottonseedate, Sucrose Polylaurate, Sucrose Polylinoleate, Sucrose Polyoleate, Sucrose Polypalmate, Sucrose Polysoyate, Sucrose Polystearate, Sucrose Ricinoleate, Sucrose Stearate, Sucrose Tetraisostearate, Sucrose Tetrastearate Triacetate, Sucrose Tribehenate, and Sucrose Tristearate.

m. Alkyl Sulfoxides

Fatty amphiphiles of the present invention further may be selected from alkyl sulfoxide compounds according to the following formula:

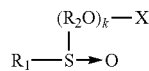

wherein $R_1$ is as described above; $R_2$ is a $C_1$-$C_5$ carbon chain which can be branched or hydroxy substituted; k is a number ranging from about 0 to about 10; and X and Y each is independently selected from hydrogen or a $C_1$-$C_4$ carbon chain which can be branched or hydroxy substituted.

Non-limiting examples of suitable alkyl sulfoxide compounds include octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, and 3-hydroxy-4-dodecoxybutyl methyl sulfoxide.

2. Surfactant

The gel network component of the present invention also comprises a secondary surfactant. As used herein, "surfactant" refers to one or more surfactants which are combined with the fatty amphiphile and oral carrier to form the gel network of the present invention. The secondary surfactant is typically water soluble or miscible in the solvent or oral carrier. The secondary surfactant may be characterized as a compound having a Hydrophilic-Lipophilic Balance ("HLB") of 6 or more and typically from about 8 to about 30. The HLB, as used herein, is the standard HLB according to Griffin, J. Soc. Cosm. Chem., vol. 5, 249 (1954). Preferably, the surfactant will be reasonably stable and foam throughout a wide pH angle.

The oral compositions of the present invention comprise secondary surfactant as part of gel network phase in an amount from about 0.01% to about 15%, preferably from about 0.1% to about 10%, and more preferably from about 0.3% to about 5%, by weight of the oral composition. In some embodiments, a diluted solution of surfactant in water is utilized. In once embodiment, the amount of surfactant is chosen based on the level of foaming desired in the oral composition and on the irritation caused by the surfactant. Once the level of surfactant is chosen, then the level of fatty amphiphile that forms a gel network is chosen. For example, in oral compositions with low level of solvents, a greater amount of fatty amphiphile may be required whereas in oral compositions with high level of solvents or water, a low level of fatty amphiphile may be chosen.

Suitable secondary surfactants include anionic, zwitterionic, amphoteric, cationic, and nonionic surfactants. In one embodiment, anionic surfactants are preferred. The secondary surfactants may be a combination of more than one type of surfactants, such as an anionic and nonionic surfactant.

Anionic surfactants useful herein include the water-soluble salts of alkyl sulfate having from 8 to 20 carbon atoms in the alkyl radical (e.g., sodium alkyl sulfate) and the water-soluble salts of sulfonated monoglycerides of fatty acids having from 8 to 20 carbon atoms. Preferred anionic surfactants for use as secondary surfactants of the present invention include sodium lauryl sulfate, sodium lauryl sarcosinate, sodium cocoyl methyl taurate, sodium monoglyceride sulfate, sodium cetaryl sulfate, potassium cocoyl glycinate, socium lauryl phosphate, sodium lauryl lactylate, sodium lauryl sulfoacetate, sodium lauroyl glutamate, sodium lauryl isethionate, sodium laureth carboxylate, sodium dodecyl benzenesulfonate, and combinations thereof. In one embodiment, sodium lauryl sulfate is a preferred secondary surfactant. Many suitable anionic surfactants are disclosed by Agricola et al., U.S. Pat. No. 3,959,458, issued May 25, 1976.

Nonionic surfactants useful herein can be broadly defined as compounds produced by the condensation of alkylene oxide groups (hydrophilic in nature) with an organic hydrophobic compound which may be aliphatic or alkyl-aromatic in nature. Nonlimiting examples of suitable nonionic surfactants include low molecular weight poloxamers (sold under the trade name Pluronic), polyoxyethylene, polyoxyethylene sorbitan esters (sold under the trade name Tweens), polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chair tertiary phosphaine oxides, lauryl glucoside (sold under the trade name Plantaren 1200 UP) and long chain dialkyl sulfoxides. Suitable nonionic surfactants with a HLB of 7 or more include sucrose laurate, sucrose cocoate, sucrose stearate; Steareth 20, 21, or 100, and PEG 20 Sorbitan Monostearate (commercially available as Tween 60).

Amphoteric surfactants suitable as a secondary surfactant in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilzing group, such as carboxylate, sulfonate, sulfate, phosphate, or phosphonate. Other suitable amphoteric surfactants are betains, such as cocamidopropyl betaine, lauryl dimethyl betaine (sold under the trade name Macat LB), cetyl dimethyl betaine, and cocoamphodiacetate. Additional amphoteric surfactants and nonionic surfactants can be found in Gieske et al., U.S. Pat. No. 4,051,234, issued Sep. 27, 1977. Examples of suitable cationic surfactants include cetyl pyridinium chloride, coamidopropyl PG dimonium chloride phosphate (Phospholipid CDM), myristylamidopropyl PG dimonium chloride phosphate (Phospholipid PTM), stearamidopropyl PG dimonium chloride phosphate (Phospholipid SV), steapyrium chloride (Catemol WPC), and other suitable cationic materials.

More than one surfactant of the above specified types may be used for the secondary surfactant of the present invention.

Another secondary surfactant may also be added to the oral carrier phase of the oral composition. This secondary surfactant is typically not part of the gel network as it does not participate in forming the gel network structure. The surfactant in the oral carrier phase may provide enhanced foaming or a different foaming profile. The surfactant added to the oral carrier phase may also aid in modifying viscosity and changing the flavor display. The addition of one or more surfactants to the oral carrier phase can be called post-added surfactants. If the surfactant is added above the phase transition temperature of the gel network, the surfactant will typically be in the gel network phase. If the surfactants is added when the temperature of the composition is below the phase transition temperature, the surfactant will typically be in the oral carrier phase and be considered a post-added surfactant.

3. Solvents

The gel network component of the present invention also comprises solvents, such as water or other suitable solvents. The solvent and the secondary surfactant together contribute to the swelling of the fatty amphiphile. This, in turn, leads to the formation and the stability of the gel network. In addition to forming the gel network, the solvent can help to keep the dentifrice composition from hardening upon exposure to air and provide a moist feel in the mouth. The solvent, as used herein, refers to suitable solvents which can be used in the place of or in combination with water in the formation of the gel network of the present invention.

Suitable solvents for the present invention include water, edible polyhydric alcohols such as glycerin, diglycerin, triglycerin, sorbitol, xylitol, butylene glycol, erythritol, polyethylene glycol, propylene glycol, and combinations thereof. Sorbitol, glycerin, water, and combinations thereof are preferred solvents.

The oral compositions of the present invention comprise solvents as part of the gel network phase in an amount suitable to achieve a gel network when combined with fatty amphiphile and secondary surfactant according to the present invention. In a preferred embodiment, the oral compositions of the present invention comprise as part of the gel network phase at least about 0.05% of a solvent, by weight of the oral composition. The solvent may be present in the oral composition in amount of from about 0.1% to about 99%, from about 0.5% to about 95%, and from about 1% to about 90%. The solvent is present in the gel network phase and may also be added or present in the oral carrier phase.

B. Oral Carrier Phase

The oral compositions of the present invention comprises an oral carrier phase. The compositions comprise an oral carrier at a level of from about 5% to about 99%, preferably from about 10% to about 90%, by weight of the compositions. The oral carriers contained in this phase is broadly described as any material in the oral composition that is not in the gel network. The oral carrier phase may also be referred to as the bulk phase or solvent phase. The oral carriers are defined broadly to include materials, such as abrasive or other non-soluble materials, that are solids (which may be described by certain analysis as not being in a particular phase). Oral carriers include cosmetic or therapeutic actives and non-actives materials.

Oral carriers suitable for the preparation of oral composition are well known. Their selection will depend on secondary considerations like taste, cost, stability, benefits desired, etc.

1. Cosmetic or Therapeutic Actives

The dentifrice composition may also comprise suitable cosmetic and/or therapeutic actives. Such actives include any material that is generally considered safe for use in the oral cavity and that provides changes to the overall appearance and/or health of the oral cavity, including, but not limited to, anti-calculus agents, fluoride ion sources, stannous ion sources, whitening agents, anti-microbial, anti-plaque agents, anti-inflammatory agents, nutrients, antioxidants, anti-viral agents, analgesic and anesthetic agents, H-2 antagonists, and mixture thereof. When present, the level of cosmetic and/or therapeutic active in the oral composition is, in one embodiment from about 0.001% to about 90%, in another embodiment from about 0.01% to about 50%, and in another embodiment from about 0.1% to about 30%, by weight of the oral composition.

The following is a non-limiting list of actives that may be used in the present invention.

a) Fluoride Ion

The present invention comprises a safe and effective amount of a fluoride compound (e.g. water soluble). The fluoride ion is present in an amount sufficient to give a fluoride ion concentration in the composition at 25° C., and/or in one embodiment can be used at levels of from about 0.0025% to about 5.0% by weight, in another embodiment from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate and many others. In one embodiment the dentifrice composition comprises stannous fluoride or sodium fluoride, as well as mixtures thereof.

b) Anticalculus Agent

Dentifrice compositions of the present invention may also comprise an anti-calculus agent, which in one embodiment may be present from about 0.05% to about 50%, by weight of the dentifrice composition, in another embodiment is from about 0.05% to about 25%, and in another embodiment is from about 0.1% to about 15%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

c) Stannous Ion

The dentifrice compositions of the present invention may include a stannous ion source. The stannous ions may be provided from stannous fluoride and/or other stannous salts. Stannous fluoride has been found to help in the reduction of gingivitis, plaque, sensitivity, and in improved breath benefits. The stannous ions provided in a dentifrice composition will provide efficacy to a subject using the dentifrice composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 3,000 ppm to about 15,000 ppm stannous ions in the total dentifrice composition. The stannous ion is present in an amount of from about 4,000 ppm to about 12,000 ppm, in one embodiment from about 5,000 ppm to about 10,000 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.001% to about 11%, by weight of the dentifrice compositions. The stannous salts may, in one embodiment, be present in an amount of from about 0.01% to about 7%, in another embodiment from about 0.1% to about 5%, and in another embodiment from about 1.5% to about 3%, by weight of the dentifrice composition.

d) Whitening Agent

A whitening agent may be included as an active in the present dentifrice compositions. The actives suitable for whitening are selected from the group consisting of alkali metal and alkaline earth metal peroxides, metal chlorites, perborates inclusive of mono and tetrahydrates, perphosphates, percarbonates, peroxyacids, and persulfates, such as ammonium, potassium, sodium and lithium persulfates, and combinations thereof. Suitable peroxide compounds include hydrogen peroxide, urea peroxide, calcium peroxide, carbamide peroxide, magnesium peroxide, zinc peroxide, strontium peroxide and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine, respectively, that the molecule is capable of providing to bleach the stain. In one embodiment the whitening agents may be present at levels from about 0.01% to about 40%, in another embodiment from about 0.1% to about 20%, in another embodiment form about 0.5% to about 10%, and in another embodiment from about 4% to about 7%, by weight of the dentifrice composition. The gel network composition may contain a whitening agent or peroxide or it may be contained in the oral carrier phase. The gel network may aid in the stabilizing of peroxides.

e) Anti-Microbial Agent

Anti-microbial agents may be included in the dentifrice compositions of the present invention. Such agents may include, but are not limited to: 5-chloro-2-(2,4-dichlorophenoxy)-phenol, commonly referred to as triclosan; 8-hydroxyquinoline and its salts; copper II compounds, including, but not limited to, copper(II) chloride, copper(II) sulfate, copper (II) acetate, copper(II) fluoride and copper(II) hydroxide; phthalic acid and its salts including, but not limited to those disclosed in U.S. Pat. No. 4,994,262, including magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; niacin preparations; zinc or stannous ion agents; nystatin; grapefruit extract; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; and mixtures of all of the above. Anti-microbial components may be present from about 0.001% to about 20% by weight of the dentifrice composition. In another embodiment the antimicrobial agents generally comprise from about 0.1% to about 5% by weight of the dentifrice compositions of the present invention.

f) Anti-Plaque Agent

The dentifrice compositions of the present invention may include an anti-plaque agent such as stannous salts, copper salts, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol in one embodiment can be present in a level of from about 0.001% to about 25%, in another embodiment from about 0.01% to about 5%, and in another embodiment from about 0.1% to about 1.5% by weight of the dentifrice composition.

g) Anti-Inflammatory Agent

Anti-inflammatory agents can also be present in the dentifrice compositions of the present invention. Such agents may include, but are not limited to, non-steroidal anti-inflammatory (NSAID) agents oxicams, salicylates, propionic acids, acetic acids and fenamates. Such NSAIDs include but are not limited to ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as ketorolac are claimed in U.S. Pat. No. 5,626,838. Disclosed therein are methods of preventing and/or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

h) Nutrients

Nutrients may improve the condition of the oral cavity and can be included in the dentifrice compositions of the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in Drug Facts and Comparisons (loose leaf drug information service), Wolters Kluer Company, St. Louis, Mo., © 1997, pps. 3-17 and 54-57.

i) Antioxidants

Antioxidants are generally recognized as useful in dentifrice compositions. Antioxidants are disclosed in texts such as Cadenas and Packer, The Handbook of Antioxidants, © 1996 by Marcel Dekker, Inc. Antioxidants useful in the present invention include, but are not limited to, Vitamin E, ascorbic acid, Uric acid, carotenoids, Vitamin A, flavonoids and polyphenols, herbal antioxidants, melatonin, aminoindoles, lipoic acids and mixtures thereof.

j) Analgesic and Anesthetic Agents

Anti-pain or desensitizing agents can also be present in the dentifrice compositions of the present invention. Analgesics are agents that relieve pain by acting centrally to elevate pain threshold without disturbing consciousness or altering other sensory modalities. Such agents may include, but are not limited to: strontium chloride; potassium nitrate; sodium fluoride; sodium nitrate; acetanilide; phenacetin; acertophan; thiorphan; spiradoline; aspirin; codeine; thebaine; levorphenol; hydromorphone; oxymorphone; phenazocine; fentanyl; buprenorphine; butaphanol; nalbuphine; pentazocine; natural herbs, such as gall nut; *Asarum*; Cubebin; Galanga; scutellaria; Liangmianzhen; and Baizhi. Anesthetic agents, or topical analgesics, such as acetaminophen, sodium salicylate, trolamine salicylate, lidocaine and benzocaine may also be present. These analgesic actives are described in detail in Kirk-Othmer, *Encyclopedia of Chemical Technology*, Fourth Edition, Volume 2, Wiley-Interscience Publishers (1992), pp. 729-737.

k) H-1 and H-2 Antagonists

The present invention may also optionally comprise selective H-1 and H-2 antagonists including compounds disclosed in U.S. Pat. No. 5,294,433.

l) Antiviral Actives

Antiviral actives useful in the present composition include any know actives that are routinely use to treat viral infections. Such anti-viral actives are disclosed in *Drug Facts and Comparisons, Wolters Kluer Company,* ©1997, pp. 402(a)-

407(z). Specific examples include anti-viral actives disclosed in U.S. Pat. No. 5,747,070, issued May 5, 1998. Said patent discloses the use of stannous salts to control viruses. Stannous salts and other anti-viral actives are described in detail in Kirk & Othmer, *Encyclopedia of Chemical Technology*, Third Edition, Volume 23, Wiley-Interscience Publishers (1982), pp. 42-71. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

m) Chelant

Chelating agents are able to complex calcium found in the cell walls of bacteria and can help to disrupt plaque by removing calcium from the calcium bridges which help hold this biomass intact. Suitable chelating agents include tartaric acid and salts thereof, citric acid and alkali metal citrates, soluble pyrophosphates, anionic polymeric polycarboxylates, and combinations thereof.

n) Anti-erosion Agents

The present compositions optionally contain anti-erosion agents such as described in commonly-assigned U.S. Pat. No. 6,685,920. Dental erosion is a permanent loss of tooth substance from the surface by the action of chemicals, such as harsh abrasives and acids, as opposed to subsurface demineralization or caries caused by bacterial action. Anti-erosion agents described therein have affinity for the tooth surface. These agents either bind to the tooth surface or form insoluble compounds or complexes on the tooth surface, thereby forming a protective film or coating on the tooth surface. As a result of these protective coatings, teeth are provided with remarkable resistance and protection against dental erosion challenges for extended periods of time following use of the composition containing these agents. Useful anti-erosion agents include polymeric mineral surface active agents such as condensed phosphorylated polymers; polyphosphonates; polycarboxylates and carboxy-substituted polymers; copolymers of phosphate- or phosphonate-containing monomers or polymers with ethylenically unsaturated monomers, amino acids, or with other polymers selected from proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) or poly(vinyl benzyl chloride); and mixtures thereof. Also useful as anti-erosion agents are metal ions selected from stannous, zinc and copper, which deposit onto teeth a highly insoluble film or precipitate of compounds or complexes formed from the reaction of the metal ions with other ingredients of the oral composition and/or components of the enamel surface.

o) Additional Actives

Additional actives suitable for use in the present invention may include, but are not limited to, insulin, steroids, natural materials, herbal and other plant derived remedies. Additionally, anti-gingivitis or gum care agents known in the art may also be included. Components which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single dentifrice composition to provide combined effectiveness. Other ingredients, such as materials providing anti-sensitivity benefits, may also be used.

Optional agents to be used include such known materials as synthetic anionic polymers, including polyacrylates and copolymers of maleic anhydride or acid and methyl vinyl ether (e.g., Gantrez), as described, for example, in U.S. Pat. No. 4,627,977, as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof. Additionally, the dentifrice composition can include a polymer carrier, such as those described in U.S. Pat. Nos. 6,682,722 and 6,589,512 and U.S. application Ser. Nos. 10/424,640 and 10/430,617.

2. Additional Oral Carriers a) Buffering Agents

The oral compositions may contain a buffering agent. Buffering agents, as used herein, refer to agents that can be used to adjust the pH of the oral compositions to a range of about pH 3.0 to about pH 10. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 0.1% to about 10%, and more preferably from about 0.3% to about 3%, by weight of the oral composition.

b) Abrasive Polishing Materials

An abrasive polishing material may also be included in the oral compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used. If the oral composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W.R. Grace & Company, Davison Chemical Division. Also preferred are the precipitated silica materials such as those marketed by the J.

M. Huber Corporation under the trade name, "Zeodent", particularly the silica carrying the designation "Zeodent 119." The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The abrasive in the oral compositions described herein is generally present at a level of from about 6% to about 70% by weight of the composition. Preferably, oral compositions contain from about 10% to about 50% of abrasive, by weight of the oral composition.

c) Titanium Dioxide

Titanium dioxide may also be added to the present composition. Titanium dioxide is a white powder which adds opacity to the compositions. Titanium dioxide generally comprises from about 0.25% to about 5%, by weight of the composition.

d) Coloring Agents

Coloring agents may also be added to the present composition. The coloring agent may be in the form of an aqueous solution, preferably 1% coloring agent in a solution of water. Pigments, pealing agents, filler powders, talc, mica, magnesium carbonate, calcium carbonate, bismuth oxychloride, zinc oxide, and other materials capable of creating a visual change to the oral compositions may also be used. Color solutions and other agents generally comprise from about 0.01% to about 5%, by weight of the composition.

e) Flavoring Components

Suitable flavoring components include oil of wintergreen, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, cranberry, chocolate, green tea, and mixtures thereof. Coolants may also be part of the flavor composition. Coolants suitable for the present compositions include the paramenthan carboxyamide agents such as N-ethyl-p-menthan-3-carboxamide (known commercially as WS-3, WS-23, WS-5), MGA, TK-10, Physcool, and mixtures thereof. Salivating agents, warming agents, numbing agents, and other optional materials can be used to deliver a signal while the oral composition is being used. A flavor composition is generally used in the oral care compositions at levels of from about 0.001% to about 5%, by weight of the oral care composition. The flavor composition will preferably be present in an amount of from about 0.01% to about 4%, more preferably from about 0.1% to about 3%, and more preferably from about 0.5% to about 2% by weight.

f) Sweetening Agents

Sweetening agents can be added to the compositions. These include saccharin, dextrose, sucrose, lactose, xylitol, maltose, levulose, aspartame, sodium cyclamate, D-tryptophan, dihydrochalcones, acesulfame, sucralose, neotame, and mixtures thereof. Various coloring agents may also be incorporated in the present invention. Sweetening agents are generally used in toothpastes at levels of from about 0.005% to about 5%, by weight of the composition.

g) Thickening Agents

Although the oral composition of the present invention is structured or thickened by the gel network, additional thickening agents, such as polymeric thickeners, may be utilized. In some embodiment, the majority of the structuring of the oral composition is from the gel network. In other embodiment, the majority of the structuring may be from a polymeric thickening agent with the gel network providing additional structuring to the oral composition.

Suitable thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can include polymeric polyether compounds, e.g., polyethylene or polypropylene oxide (M.W. 300 to 1,000,000), capped with alkyl or acyl groups containing 1 to about 18 carbon atoms.

A suitable class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly the carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220; 5,242,910; and 4,443,430.

Thickening agents in an amount from about 0% to about 15%, or from about 0.01% to about 6%, in another embodiment from about 0.1% to about 5%, by weight of the total oral composition, can be used. The oral composition can be essentially free of thickening agents if it is structured or thickened by the gel network. In other embodiments, a small amount of a thickening agent, such as from about 0.01% to about 1% or from about 0.05% to about 0.5%, can be used in combination with the gel network. The specific amount of thickening agent will be selected based on the desired rheology and function of the gel network.

h) Humectant

A humectant can help to keep the dentifrice composition from hardening upon exposure to air and provide a moist feel in the mouth. A solvent is required in the gel network phase. A humectant or additional solvent may be added to the oral carrier phase. Suitable humectants for the present invention include water, edible polyhydric alcohols such as glycerin, sorbitol, xylitol, butylene glycol, polyethylene glycol, propylene glycol, and combinations thereof. Sorbitol, glycerin, water, and combinations thereof are preferred humectants. The humectant may be present in an amount of from about 0.1% to about 99%, from about 0.5% to about 95%, and from about 1% to about 90%. The oral carrier phase can also be made without a humectant. The oral composition structured with a gel network instead of typical polyermic thickener, or with low levels of polymeric thickeners, may not require a humectant or may allow for lower levels of humectants. The oral composition with the gel network will typically provide a moist mouthfeel and/or not become dried out when exposed to air. A gel network composition could be free of humectants or anhydrous for use as a denture adhesive composition.

i) Sufactants

An additional surfactant may be added to the oral carrier phase of the oral composition. This may be the same surfactant that is added to the gel network phase or a different surfactant. A surfactant may aid in the cleaning or foaming of the oral composition. Suitable surfactants are described above in the gel network section.

C. Process of Making an Oral Composition

An aspect of the invention relates to a process of making an oral composition of the present invention. The process of making an oral composition comprises (a) heating the fatty amphiphile, a secondary surfactant, and solvent to a temperature sufficient to allow partitioning of the secondary surfactant and the solvent into the fatty amphiphile, typically at least about 5 C above the melt temperature of the fatty amphiphile, and (b) cooling the pre-mix below the melt temperature of the fatty amphiphile to form a gel network. The oral carrier ingredients may be added at any time during the process such as before heating, during heating, before cooling, or after cooling. It may be desired to add certain oral carrier ingredients after heating, such as the flavor.

In one embodiment of the present invention, the gel network phase of the present invention may be prepared by heating the fatty amphiphile, the secondary surfactant, and solvent to a level of at least 5 C above the melt temperature of the fatty amphiphile. The heating may be in the range of about 50° C. to about 90° C., typically from about 70 C to about 90 C. Preferably, the materials are before heating, during heating, after heating, during cooling, and after cooling. After being heated, the mixture is cooled to a level in the range of about 20° C. to about 35° C. Depending upon the size of the batch, equipment, specific materials, and time, the mixture may be cooled by mixing only, by an ice bath, or by passing the mixture through a heat exchanger. As a result of this cooling step, the fatty amphiphile and the secondary surfactant crystallize to form a crystalline gel network.

Alternative methods of preparing the gel network component include sonication and/or milling of the fatty amphiphile, the secondary surfactant, and solvent, while these components are heated, to reduce the particle size of the melted fatty amphiphile phase. This results in an increase in surface area of the fatty amphiphile phase, which allows the secondary surfactant and the solvent to swell the fatty amphiphile phase. Another suitable variation in preparing the gel network includes heating and mixing the fatty amphiphile and the secondary surfactant first, and then adding that mixture to the solvent.

The gel network can be used by itself to structure or thicken the oral composition to provide the desired rheology. The gel network can also be used in combination with other thickening materials. The gel network may be formulated to produce a dentifrice: having rheology enabling the solids and other particles to be suspended, easily dispensed from a container, stand-up on a toothbrush head once the dentifrice is dispensed, low or no stringiness when dispensed, ease of dispersion in the mouth, and other rheological properties desired of a dentifrice.

The viscosity of the dentifrice is typically from about 8 to about 100 BKU, from about 15 to about 80 BKU, and commonly from about 15 to about 50 BKU. As used herein, BKU is the unit of viscosity. The viscometer is Brookfield viscometer, Model ½ RVT (½ spring strength), with a Brookfield "Helipath" stand. The spindle is a conventional "E-series" T-shaped spindle. The viscometer is placed on the Helipath stand and leveled via spirit levels. The E spindle is attached, and the viscometer is set to 2.5 RPM while it is running. The viscosity is measured after 1 minute and the temperature is constant at 25 C. The dentifrice composition will have an acceptable rheology, good texture, pleasing aesthetics, and a deaerated specific gravity from about 0.9 to about 1.8 and can be from about 1.1 to about 1.6.

D. Method of Use

The compositions of the present invention are used in a conventional manner for cleansing the teeth. Generally, a method of using a dentifrice to cleanse the teeth comprises applying the composition of the present invention to a toothbrush, brushing the teeth for a period of time, and then rinsing the dentifrice from the mouth. From about 0.01 to about 3 grams of toothpaste is typically used.

NON-LIMITING EXAMPLES

The oral compositions illustrated in the following Examples illustrate specific embodiments of the oral compositions of the present invention, but are not intended to be limiting thereof. Other modifications can be undertaken by the skilled artisan without departing from the spirit and scope of this invention.

ORAL COMPOSITION EXAMPLES

The following Examples illustrate specific embodiments of the oral composition utilizing gel networks.

In examples 1-4, a gel network is formed in Step 1 and then other oral carriers are added to the gel network. For examples 1-4, Step 1 ingredients are combined in a mixing vessel and heated to between about 75 C to about 90 C while being mixed. The mixture is further mixed and then cooled to about 25 C to form a crystalline gel network. Once the gel network is formed, the Step 2 ingredient are added either individually or a premix and mixed to form the oral composition. As is typical, the flavor is added as the final ingredient to minimize volatile loss.

Examples 1-4

| Premix | Ingredients | Example 1 | Example 2 | Example 3 | Example 4 |
|---|---|---|---|---|---|
| 1 | Water | 31.15% | | 25.70% | 31.88% |
| 1 | Glycerin (@99.7%) | 38.00% | 69.45% | | 44.00% |
| 1 | Sorbitol (@ 70%) | | | 20.0% | |
| 1 | Sodium Lauryl Sulfate (@28%) | 3.00% | 3.50% | 5.00% | 7.00% |
| 1 | Cetyl Alcohol | 1.90% | 1.50% | 3.00% | 2.20% |
| 1 | Stearyl Alcohol | 1.90% | 1.50% | 3.00% | 2.20% |
| 2 | Sodium Fluoride | 0.24% | 0.24% | | 0.24% |
| 2 | Disodium MonoFluoro Phosphate (MFP) | | | 0.80% | |
| 2 | Calcium Carbonate (ground limestone 2531) | | | 40.00% | |
| 2 | Silica | 17.00% | 17.00% | | 5.00% |
| 2 | Sodium Acid Pyrophosphate | 1.00% | 1.00% | | |
| 2 | Tetra Sodium Pyrophosphate | 3.85% | 3.85% | 1.00% | 6.00% |
| 2 | Sodium Saccharin | 0.46% | 0.46% | 0.50% | 0.48% |
| 2 | Titanium Dioxide | 0.50% | 0.50% | | |
| | Peppermint Flavor | 1.00% | 1.00% | 1.00% | 1.00% |

In examples 5-14, the gel network is formed as the oral composition is made. All of the materials listed in Examples 5-14 can be added at any time as long as the fatty amphiphile, secondary surfactant, and solvent needed to make the gel network are added prior to the heating step and cooling step. In these embodiments, the flavor is also added as the final ingredient.

Examples 5-9

| Ingredients | Example 5 | Example 6 | Example 7 | Example 8 | Example 9 |
|---|---|---|---|---|---|
| Water | qs | qs | Qs | qs | qs |
| Sorbitol (@ 70%) | 50.00% | 50.00% | 50.00% | 50.00% | 50.00% |
| Cocamidopropyl Betaine (@ 30%) | 4.00% | | | | |

| Ingredients | Example 5 | Example 6 | Example 7 | Example 8 | Example 9 |
|---|---|---|---|---|---|
| Sodium Alkyl C10-16 Glyceryl Sulfonate (@47.5%) | | 2.53% | | | |
| Sarcosinate LN30 (@ 30%) | | | 4.00% | | |
| Sodium Methyl Cocoyl Taurate (@ 30%) | | | | 4.00% | |
| Cetyl Pyridinium Chloride | | | | | 1.20% |
| Cetyl Alcohol | 2.00% | 2.00% | 2.00% | 2.00% | 2.00% |
| Stearyl Alcohol | 2.00% | 2.00% | 2.00% | 2.00% | 2.00% |
| Sodium Fluoride | 0.24% | 0.24% | 0.24% | 0.24% | 0.24% |
| Silica | 17.00% | 17.00% | 17.00% | 17.00% | 17.00% |
| Sodium Acid Pyrophosphate | 1.00% | 1.00% | 1.00% | 1.00% | 1.00% |
| Tetra Sodium Pyrophosphate | 3.85% | 3.85% | 3.85% | 3.85% | 3.85% |
| Sodium Saccharin | 0.46% | 0.46% | 0.46% | 0.46% | 0.46% |
| Titanium Dioxide | 0.50% | 0.50% | 0.50% | 0.50% | 0.50% |
| Peppermint Flavor | 1.00% | 1.00% | 1.00% | 1.00% | 1.00% |

Examples 10-14

| Ingredients | Example 10 | Example 11 | Example 12 | Example 13 | Example 14 |
|---|---|---|---|---|---|
| Water | qs | qs | qs | qs | qs |
| Sorbitol (@ 70%) | 50.00% | 50.00% | 50.00% | 50.00% | 50.00% |
| Sodium Lauryl Sulfate (@ 28%) | 2.00% | 4.00% | 4.00% | 4.00% | 4.00% |
| Cocamidopropyl Betaine (@ 30%) | 2.00% | | | | |
| Cetyl Alcohol | 2.00% | | 1.50% | 1.50% | 1.50% |
| Stearyl Alcohol | 2.00% | 1.00% | 1.50% | 1.50% | 1.50% |
| Behenyl Alcohol (Lanette-22) | | 2.50% | | | |
| Carboxy Methyl Cellulose | | | 0.50% | | |
| Xanthan gum (Keltrol-F) | | | | 0.50% | |
| Iota Carrageenan | | | | | 0.50% |
| Sodium Fluoride | 0.24% | 0.24% | 0.24% | 0.24% | 0.24% |
| Silica | 17.00% | 17.00% | 17.00% | 17.00% | 17.00% |
| Sodium Acid Pyrophosphate | 1.00% | 1.00% | 1.00% | 1.00% | 1.00% |
| Tetra Sodium Pyrophosphate | 3.85% | 3.85% | 3.85% | 3.85% | 3.85% |
| Sodium Saccharin | 0.46% | 0.46% | 0.46% | 0.46% | 0.46% |
| Titanium Dioxide | 0.50% | 0.50% | 0.50% | 0.50% | 0.50% |
| Peppermint Flavor | 1.00% | 1.00% | 1.00% | 1.00% | 1.00% |

In Examples 15-18, the gel network is formed in Step 1 and the other ingredients added as Step 2 with the flavor added last when the batch is cool.

Examples 15-18

| Step | Ingredients | Example 15 | Example 16 | Example 17 | Example 18 |
|---|---|---|---|---|---|
| 1 | Water | Qs | qs | qs | qs |
| 1 | Sorbitol (@ 70%) | 50% | 50% | 50% | 50% |
| 1 | Phospholipid PTM (@30%) | | | 1.50% | 2.50% |
| 1 | Sodium Lauryl Sulfate (@28%) | 2.50% | 1.50% | | |
| 1 | Cetyl Alcohol | 3.00% | 2.00% | 2.00% | 2.00% |
| 1 | Stearyl Alcohol | 3.00% | 2.00% | 2.00% | 2.00% |
| 2 | Sodium Fluoride | 0.24% | 0.24% | 0.24% | 0.24% |
| 2 | Sodium Lauroyl Glutamate(@30%) | 2.00% | | | 2.00% |
| 2 | Cetyl Betaine | | 2.50% | 2.50% | |
| 2 | Silica | 17.00% | 17.00% | 17.00% | 17.00% |
| 2 | Sodium Acid Pyrophosphate | 1.00% | 1.00% | 1.00% | 1.00% |
| 2 | Tetra Sodium Pyrophosphate | 3.85% | 3.85% | 3.85% | 3.85% |
| 2 | Sodium Saccharin | 0.46% | 0.46% | 0.46% | 0.46% |
| 2 | Titanium Dioxide | 0.50% | 0.50% | 0.50% | 0.50% |
| | Peppermint Flavor | 1.00% | 1.00% | 1.00% | 1.00% |

In other examples, a concentrated dentifrice may be formed. The concentrated dentifrice is structured by a gel network. After packaging, a solvent, preferably water, could be added to the concentrated dentifrice to form dentifrice with typical levels of actives and rheology for brushing. An oral care composition structured by a gel network retains a homogeneous structure when diluted with excess amounts of water or other solvents. This is in contrast to typical polymer thickened oral compositions. The concentrated dentifrice may be formulated to contain twice, three times, four times, five times, or more of the amount of active or solid materials as in typical dentifrice compositions. The concentrated dentifrice can be diluted prior to use or during use.

More than one gel network composition may be used in an oral composition. Two or more gel network compositions can be used to structure the oral composition. Alternatively, one gel network composition can be used to structure the oral composition and a second gel network to aid in the delivery of a material, such as a flavor. Two or more gel network compositions may also be desired to achieve certain visual appearances such as striped or multicolor products. It may be desired to have more than one gel network composition in an oral care composition to provide color stability, flavor delivery, or incorporate incompatible materials. The gel network composition may also aid in sequestering flavors or coolants or other large organic materials for various types of flavor displays. The gel network composition may also aid in the delivery of cationic, anionic, hydrophilic, hydrophobic, insoluble, or soluble materials or combinations thereof. This may be beneficial in delivering incompatible materials. The gel network composition may also aid in targeting the delivery, release, or extended delivery of materials such as actives, flavors, or other materials for aesthetic reasons or other benefits.

Analytical Methods and Examples

The following methods are used to identify gel networks.
Differential Scanning calorimetry Method The chain melt temperature of the layer in the gel network comprising the one or more fatty amphiphiles (i.e., the melt transition temperature for the gel network) may be obtained using differential scanning calorimetry according to the following method. Utilizing a TA Instruments Q100 DSC, approximately 50 mg of the gel network pre-mix or the final oral composition containing the gel network is placed into a stainless steel high volume DSC pan. The sample, along with an empty reference pan is placed into the instrument. The samples are analyzed using the following conditions/temperature program: Nitrogen Purge, Equilibrate @ 5.00° C.

until an isothermal is reach for 2.00 min Ramp the temperature at a rate of 3.00° C./min to 90.00° C. Each sample is analyzed in duplicate. The resulting DSC data is analyzed using TA Instruments Universal Analysis Software.

The use of DSC to measure the melt transition temperature for gel networks is further described by T. de Vringer et al., *Colloid and Polymer Science*, vol. 265, 448-457 (1987); and H. M. Ribeiro et al., *Intl. J. of Cosmetic Science*, vol. 26, 47-59 (2004).

X-Ray Analysis Method

Small-angle x-ray scattering ("SAXS") as used to resolve periodic structures in mesophases is essentially an x-ray diffraction technique. It is used in conjunction with conventional wide-angle x-ray diffraction ("WXRD") to characterize aggregate structures such as micelles, gel networks, lamella, hexagonal and cubic liquid crystals. The different mesophases that show periodic structures can be characterized by the relative positions (d-spacing) of their reflections as derived from the Bragg equation ($d=\lambda/2 \sin \theta$) where d represents the interplanar spacing, $\lambda$ the radiation wavelength and $\theta$ the scattering (diffraction) angle.

The one dimensional lamella gel network phase is characterized by the ratio of the interplanar spacings $d_1/d_1$, $d_1/d_2$, $d_1/d_3$, $d_1/d_4$, $d_1/d_5$ having the values 1:2:3:4:5 etc. in the SAXS region (long-range order) and one or two invariant reflection(s) in the WXRD region (short-range) centered around 3.5 and 4.5 Å over a broad halo background. Other mesophases (e.g. hexagonal or cubic) will have characteristically different d-spacing ratios.

WXRD data are collected in transmission mode on a Stoe STADI-P diffractometer equipped with an image plate position-sensitive detector. The specimen is positioned between two milar films in the sample holder and placed in the path of the x-ray beam. The IP detector has a solid angle of about 120° $2\theta$ and records diffracted x-ray beams simultaneously. Data are collected and analyzed using the XPOW software.

SAXS data are collected on Rigaku rotating anode generator with a fine focus filament equipped with a HI-STAR 2-dimensional area detector from Bruker-AXS. The setup has an evacuated chamber, which houses the specimen, conjoined with an evacuated tube leading to the detector to reduce air scatter. The specimen sample holder consists of copper plates with small rectangular cavities to hold the fluid-like material and also allow the transmission of the x-ray beam. The openings to the cavities are sealed with kapton windows to provide leak-free environment under vacuum. The 2-D data are azimuthally integrated and reduced to intensity versus scattering vector (q) or its d equivalent by a combination of GADDS software and in-house software modules implementing known techniques on the Igor platform.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
  a) a gel network phase comprising:
    i) from about 0.1% to about 20%, by weight of the composition, of a fatty amphiphile wherein the fatty amphiphile has a melting point of at least about 45° C.;
    ii) from about 0.1% to about 10%, by weight of the composition, of a surfactant;
      wherein the weight ratio of fatty amphiphile to surfactant is from about 2:1 to about 10:1;
  b) an oral carrier phase comprising:
    i) fluoride compound selected from the group consisting of stannous fluoride, sodium fluoride, potassium fluoride, amine fluoride, sodium monofluorophosphate, and combinations thereof;
    ii) from about 0.5% to about 10%, by weight of the composition, of a peroxide compound
    iii) from about 1% to about 90% water;
    iv) flavor;
    v) an abrasive polishing material;
      wherein the dentifrice composition foams when used in a conventional manner for cleansing teeth.

2. The dentifrice composition of claim 1 wherein the fatty amphiphile is a combination of cetyl alcohol and stearyl alcohol; the surfactant is an anionic surfactant; and the peroxide compound is hydrogen peroxide.

3. The dentifrice composition of claim 1 wherein the oral carrier phase further comprises potassium nitrate.

4. A dentifrice composition comprising:
  a) a gel network phase comprising:
    i) a fatty amphiphile;
    ii) a surfactant;
      wherein the weight ratio of fatty amphiphile to surfactant is from about 1:1 to about 10:1;
  b) an oral carrier phase comprising:
    i) a fluoride compound selected from the group consisting of stannous fluoride, sodium fluoride, potassium fluoride, amine fluoride, sodium monofluorophosphate, and combinations thereof;
    ii) a peroxide compound;
    iii) water;
    iv) a flavor;
      wherein the dentifrice composition foams when used in a conventional manner for cleansing teeth.

5. The dentifrice composition of claim 4 wherein the fatty amphiphile is a combination of cetyl alcohol and stearyl alcohol.

6. The dentifrice composition of claim 4 wherein the surfactant comprises an anionic surfactant.

7. The dentifrice composition of claim 6 wherein the anionic surfactant comprises sodium lauryl sulfate.

8. The dentifrice composition of claim 4 wherein the peroxide compound is hydrogen peroxide and wherein the composition comprises from about 0.5% to about 10%, by weight, hydrogen peroxide.

9. The dentifrice composition of claim 4 wherein the oral carrier phase further comprises an abrasive polishing material.

10. The dentifrice composition according to claim 4 wherein the gel network phase provides the dentifrice composition with a desired rheology without the use of a polymeric thickening agent.

11. The dentifrice composition according to claim 4 wherein the gel network phase is used to structure the dentifrice composition and wherein a rheology of the dentifrice composition enables the dentifrice composition to be easily dispensed from a container and stand-up on a toothbrush head after the composition is dispensed.

12. The dentifrice composition according to claim 4 wherein the dentifrice composition comprises a viscosity from about 15 to about 50 BKU.

13. The dentifrice composition of claim 4 wherein the dentifrice composition comprises a deaerated specific gravity from about 1.1 to about 1.6.

14. The dentifrice composition of claim 4 wherein the dentifrice composition further comprises a moist feeling in the mouth when used in the conventional manner for cleansing teeth.

15. The dentifrice composition of claim 4 wherein the rheology of the dentifrice composition enables the composition to comprise low or no stringiness when dispensed.

16. The dentifrice composition of claim 4 wherein the dentifrice composition can be easily dispersed in a mouth and can be rinsed from the mouth when used in the conventional manner for cleansing teeth.

17. The dentifrice composition of claim 4 wherein the oral carrier phase further comprises potassium nitrate.

18. An oral care composition comprising:
a) a gel network phase comprising:
  i) a fatty amphiphile;
  ii) a surfactant;
  iii) a solvent;
b) an oral carrier phase comprising water;
  wherein the gel network phase is used to structure the composition;
  wherein the gel network phase provides the composition with a desired rheology without the use of a polymeric thickening agent;
  wherein the composition can be easily dispersed in a mouth and can be rinsed from the mouth when used in the conventional manner for cleansing teeth; and
  wherein the composition further comprises a moist feeling in the mouth when used in the conventional manner for cleansing teeth.

19. The oral care composition of claim 18 wherein the oral carrier phase further comprises from about 0.5% to about 10%, by weight of the composition, hydrogen peroxide.

20. A method of whitening teeth comprising applying to teeth a safe and effective amount of the composition according to claim 19.

21. The oral care composition of claim 18 wherein the composition is a dentifrice composition and the oral carrier phase further comprises an abrasive and a fluoride compound selected from the group consisting of stannous fluoride, sodium fluoride, potassium fluoride, amine fluoride, sodium monofluorophosphate, and combinations thereof;
  wherein the dentifrice composition foams when used in a conventional manner for cleansing teeth; and
  wherein the rheology of the dentifrice composition enables the dentifrice composition to be easily dispensed from a container and stand-up on a toothbrush head after the composition is dispensed; and
  wherein the rheology of the dentifrice composition enables the composition to comprise low or no stringiness when dispensed.

22. A method of removing plaque from teeth comprising applying to teeth a safe and effective amount of the dentifrice composition according to claim 21.

23. The oral care composition of claim 18 wherein the oral carrier phase further comprises potassium nitrate.

* * * * *